(12) United States Patent
Lee et al.

(10) Patent No.: US 7,936,106 B2
(45) Date of Patent: May 3, 2011

(54) SURFACE ACOUSTIC WAVE SENSOR DEVICE

(75) Inventors: Hun Joo Lee, Seoul (KR); Soo Suk Lee, Suwon-si (KR); Yeol Ho Lee, Seoul (KR); Ki Eun Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 114 days.

(21) Appl. No.: 12/544,515

(22) Filed: Aug. 20, 2009

(65) Prior Publication Data

US 2010/0314967 A1   Dec. 16, 2010

(30) Foreign Application Priority Data

Jun. 11, 2009  (KR) .......................... 10-2009-0052049

(51) Int. Cl.
  *H03H 9/25*  (2006.01)
  *H01L 41/053*  (2006.01)
  *H01L 41/113*  (2006.01)
(52) U.S. Cl. ..................... 310/313 R; 310/338; 310/348
(58) Field of Classification Search .............. 310/313 R, 310/338, 348
See application file for complete search history.

(56) References Cited

U.S. PATENT DOCUMENTS

| | | | | |
|---|---|---|---|---|
| 3,395,295 A * | 7/1968 | Crane | ...................... | 310/323.21 |
| 3,515,911 A * | 6/1970 | Byram et al. | ............. | 310/313 R |
| 3,673,474 A * | 6/1972 | White et al. | ................... | 318/116 |
| 3,917,401 A * | 11/1975 | Stolwyk | .......................... | 355/53 |
| 4,595,338 A * | 6/1986 | Kolm et al. | ..................... | 416/81 |
| 6,543,274 B1 | 4/2003 | Herrmann et al. | | |
| 7,638,928 B2 * | 12/2009 | Palanduz et al. | ............. | 310/328 |
| 2003/0000291 A1 * | 1/2003 | Kolosov et al. | ............. | 73/61.52 |
| 2005/0226773 A1 | 10/2005 | Liu | | |

FOREIGN PATENT DOCUMENTS

| | | |
|---|---|---|
| KR | 10-2007-0072224 A | 7/2007 |
| KR | 10-2008-0101630 A | 11/2008 |

* cited by examiner

*Primary Examiner* — Thomas M Dougherty
(74) *Attorney, Agent, or Firm* — Cantor Colburn LLP

(57) ABSTRACT

Provided herein is a surface acoustic wave (SAW) sensor device including a surface acoustic wave sensor and an oscillator corresponding to the surface acoustic wave sensor. A horizontal plane defined by the oscillator is inclined at a predetermined angle with respect to a horizontal plane defined by the surface acoustic wave sensor. The predetermined angle is greater than zero degrees.

14 Claims, 5 Drawing Sheets

SURFACE ACOUSTIC WAVE SENSOR DEVICE

CROSS-REFERENCE TO RELATED APPLICATION

This application claims priority to Korean Patent Application No. 2009-52049, filed on Jun. 11, 2009, and all the benefits accruing therefrom under 35 U.S.C. §119, the content of which in its entirety is herein incorporated by reference.

BACKGROUND

1) Field

The general inventive concept relates to a surface acoustic wave ("SAW") sensor device and, more particularly to a SAW sensor device that provides advantages which include, but are not limited to, substantially reduced sample loss, signal interference and noise.

2) Description of the Related Art

A surface acoustic wave sensor is a device that senses a target material, e.g., an analyte using a surface acoustic wave ("SAW.") In general, a SAW is a mechanical wave generated from movement of particles due to thermal, mechanical or electrical power, for example, but not due to an electromagnetic wave. As a result, a majority of vibrational energy in the SAW is concentrated at a surface of a medium through which the SAW is transmitted.

Generally, the SAW sensor is disposed on a substrate made of a piezoelectric material, and includes a receptor attached thereto. The receptor specifically binds to a desired target material on a surface of the sensor. When a solution containing the target material flows to the SAW sensor, signals, such as wavelength, for example, are changed by mechanical, chemical and/or electrical reactions of the target material with the receptor. Accordingly, properties of the target material are quantified by monitoring changes in the signals.

The SAW sensor is particularly sensitive to changes pressure of a fluid and/or viscosity or density of a medium, as well as mass change on the surface. As a result, precise control of the fluid is very important to minimize noise, which is a signal change due to factors other than the mass change, for example.

In a typical SAW sensor, an oscillation technique of applying an output signal, emitted from an output inter-digital transducer ("IDT"), to an input IDT of the SAW sensor is used to generate a SAW in an electrode of the SAW sensor. In addition, a technique of generating a specific frequency outside the SAW sensor includes applying the specific frequency to the input IDT, and plotting an emitted output signal of the SAW sensor.

Although the oscillation technique provides increased sensitivity, this technique requires that an oscillator be installed in the SAW sensor. Moreover, the oscillator is generally in contact with and parallel to the SAW sensor.

In addition, large changes may occur in the SAW sensor, due to pressure gradients needed for fluid flow. Thus a plurality of the SAW sensors is typically driven in one chamber to reduce errors caused by the pressure gradients. Additionally, various tests may be rapidly conducted when one chamber includes a plurality of SAW sensors, because errors caused by a washing deviation are reduced and various target materials can be detected from one sample.

As a result, however, a plurality of SAW sensors are required and, since the oscillator is larger than the SAW sensors of the plurality of SAW sensors, a distance between the SAW sensors is limited due to the large size of the oscillator compared to the SAW sensors. Further, as the distance between the SAW sensors and the oscillator increases, losses of the sample increase and substantially interference of signals and/or noise is generated.

SUMMARY

Exemplary embodiments provide a surface acoustic wave ("SAW") sensor device which that provides substantially reduced loss of a sample, interference of signal, and noise by effectively minimizing a distance between SAW sensors during installation of an oscillator.

In addition, exemplary embodiments provide a SAW sensor device having an oscillator installed not parallel to a SAW sensor therein, thereby further reducing the distance between the SAW sensors.

According to an exemplary embodiment, a SAW sensor device includes a SAW sensor and an oscillator corresponding to the SAW sensor. A horizontal plane defined by the oscillator inclined at a predetermined angle with respect to a horizontal plane defined by SAW sensor. The predetermined angle is greater than zero (0) degrees.

The SAW sensor device may include two or more of the surface acoustic wave sensors and two or more of the oscillators. In addition, each oscillator of the two or more oscillators may correspond to a surface acoustic wave sensor of the two or more surface acoustic wave sensors.

According to an alternative exemplary embodiment, a method of fabricating a SAW sensor device includes: providing a surface acoustic wave sensor array substrate; arranging surface acoustic wave sensors on the surface acoustic wave sensor array substrate; connecting oscillators to a top plate, the top plate disposed substantially parallel to the surface acoustic wave sensor array substrate; and connecting each of the surface acoustic wave sensors to a corresponding one of the oscillators. A horizontal plane defined by each of the oscillators is inclined at a predetermined angle with respect to a horizontal plane defined by each of the surface acoustic wave sensors, the predetermined angle being greater than zero degrees.

BRIEF DESCRIPTION OF THE DRAWINGS

The above and other aspects, features and advantages of the present invention will become more apparent by describing in further detail exemplary embodiments thereof with reference to the accompanying drawings, in which.

DETAILED DESCRIPTION

Figure 1:
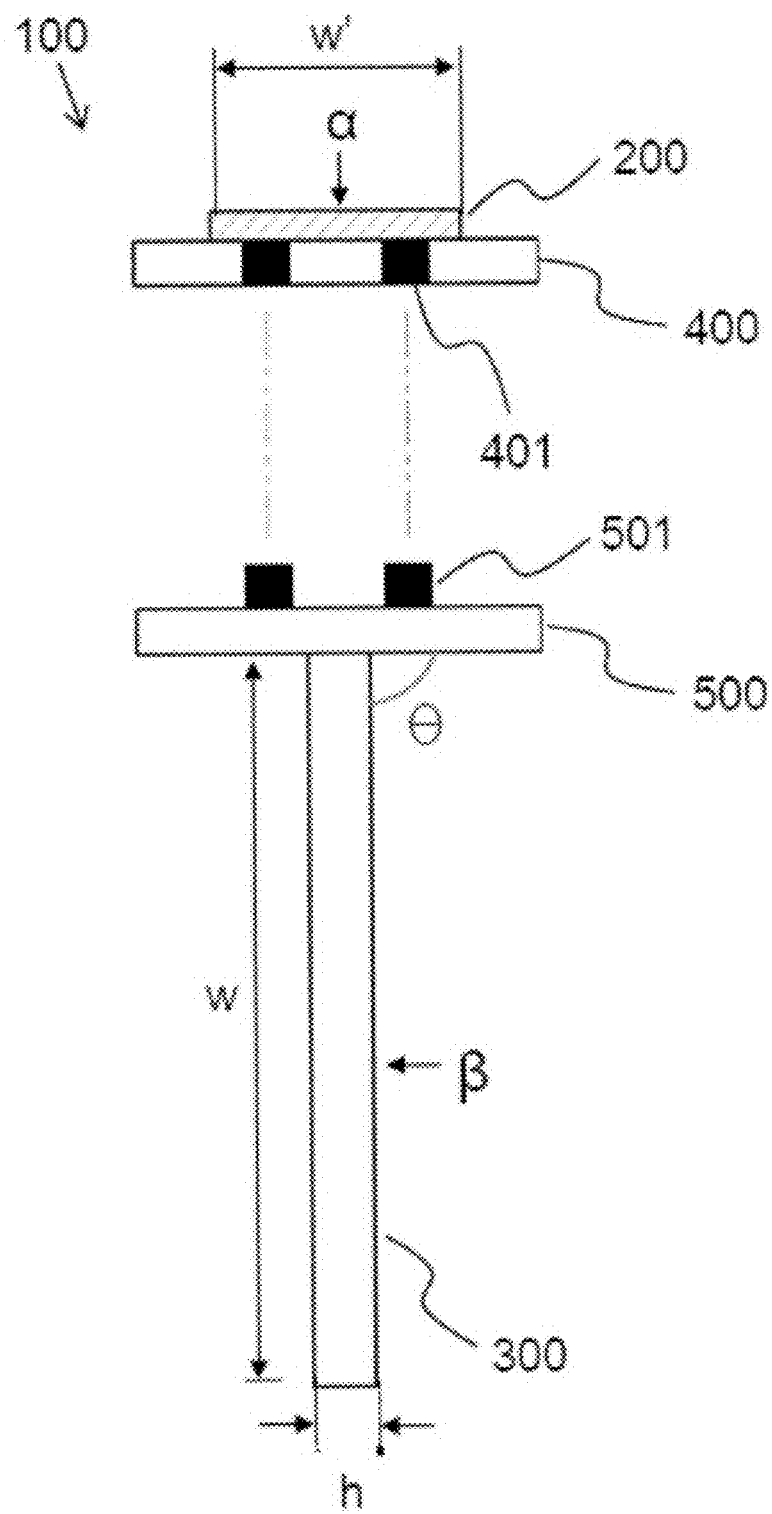
FIG. 1 is a partial cross-sectional view of an exemplary embodiment of a surface acoustic wave ("SAW") sensor device.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims Hereinafter, exemplary embodiments of the present invention will be described in further detail with reference to the accompanying drawings.

A surface acoustic wave ("SAW") sensor device according to an exemplary embodiment includes one or more SAW sensors and one or more oscillators corresponding to the SAW sensors. In addition, in an exemplary embodiment a horizontal plane defined by a given oscillator is not parallel to a horizontal plane defined by a corresponding SAW sensor. Instead, the horizontal plane defined by the oscillator is inclined at a predetermined angle with respect to the horizontal plane defined by the SAW sensor, as will be described in greater detail below.

FIG. 1 is a partial cross-sectional view of an exemplary embodiment of a SAW sensor device.

Referring to FIG. 1, a SAW sensor device 100 according to an exemplary embodiment includes a SAW sensor 200 and an oscillator 300. More specifically, a horizontal plane β defined by the oscillator 300 is inclined at a predetermined degree angle θ, which is greater than zero (0) degrees, with respect to a horizontal plane a defined by the SAW sensor 200. Accordingly, the parallel horizontal plane β is not parallel to the horizontal plane α.

In addition, a width w of the oscillator 300 is greater than a width w' of the SAW sensor 200, as shown in FIG. 1. Thus, if the oscillator 300 were to be installed parallel to the SAW sensor 200, e.g., if the predetermined angle were zero (0) degrees, a length of the SAW sensor device would be restricted due to the width w of the oscillator 300. As a result, a large amount dead volume would exist in the saw sensor device 100, and a substantial portion of a sample would not pass through the SAW sensor 200, e.g., a substantial portion of the sample would be lost and would subsequently not be analyzed.

In contrast, however, the oscillator 300 according to an exemplary embodiment is inclined at the predetermined angle θ, and the width w with which the oscillator 300 occupies is substantially reduced.

However, as the predetermined angle θ between the horizontal plane β of the oscillator 300 and the horizontal plane a of the SAW sensor 200 approaches 180 degrees) (°), it becomes increasingly difficult to decrease the width w of the oscillator. Thus, in an exemplary embodiment, the predetermined angle θ may be, for example, from about 30° to about 270° or, in an alternative exemplary embodiment, about 90°±30°, e.g., from about 60° to about 120°.

As shown in FIG. 1, the oscillator 300 is substantially perpendicular to the horizontal plane α of the SAW sensor 200, and the width w with which the oscillator 300 substantially occupies corresponds to a height h of the oscillator 300, and thus the oscillator 300 occupies less area than the width w' of the SAW sensor 200, e.g., a value of the height h of the oscillator 300 is substantially less than a value of the width w' of the SAW sensor 200.

As a result, in the SAW sensor device 100 according to an exemplary embodiment, the distance between the SAW sensors 200 is substantially reduced by installing the oscillator 300 at the predetermined angle θ, and thus an amount of a sample solution containing target materials (such as a patient specimen, for example) required for analysis is substantially reduced. Alternatively, for a given amount of the sample, solution, an amount that is lost is substantially reduced and/or effectively minimized in the SAW sensor device 100 according to an exemplary embodiment.

Further, the SAW sensor device 100 may include an oscillation technique with high sensitivity and, accordingly, a plurality of the SAW sensors 200 is disposed in one device, e.g., in a single SAW sensor device 100, thereby substantially reducing deviations due to pressure and/or washing, as well as a substantially reduction in noise. Moreover, the SAW sensor device 100 is fabricated to have a small size through high-integration of the device, e.g. through using the plurality of SAW sensors 200 inclined at the predetermined angle θ, such that a height h of each of the oscillators 300 is substantially less than a corresponding width w' of the SAW sensors 200.

In an exemplary embodiment, the SAW sensor 200 and the oscillator 300 may be connected to each other via separate connecting portions 400 and 500, as shown in FIG. 1, but alternative exemplary embodiments are not limited thereto, e.g., in an alternative exemplary embodiment, the SAW sensor and 200 and the oscillator 300 may be directly connected to each other without requiring the connecting portions 400 and 500.

The connecting portions 400 and 500 include connectors 401 and 501, respectively, for electrical connections thereto. In an exemplary embodiment, the connector 401, disposed on the connecting portion 400, is connected to the SAW sensor 200, while the connector 501, disposed on the connecting portion 500, is to the oscillator 300.

Meanwhile, receptors (not shown) bound to target materials, e.g., detection object materials, are supplied to a surface of the SAW sensor 200.

The receptors may include, but are not limited to, proteins, antigens, antibodies, enzymes, deoxyribonucleic acids ("DNAs"), ribonucleic acids ("RNAs"), peptide nucleic acids ("PNAs"), e.g., artificial DNAs, cells and olfactories, and the target materials specifically bound to the receptors may include, but are not limited to, bio molecules such as proteins, antibodies, antigens, DNAs, RNAs, bacteria, animal cells, viruses and tissues, or toxins generated from the materials described above.

In an exemplary embodiment, the oscillator 300 is a part of a radio frequency ("RF") circuit, and generates a sine-wave signal having a specific frequency. Moreover, the oscillator 300 converts direct current ("DC") energy into alternating current ("AC") energy. Unlike an amplifier, a frequency signal may be detected in a narrow band using only an output port, e.g., without requiring an input port.

In another exemplary embodiment, the SAW sensor device 100 may include two or more of the SAW sensors 200. For example, a saw sensor device according to an alternative exemplary embodiment includes a SAW sensor array substrate including two or more SAW sensors disposed thereon, as will be described in further detail below.

FIG. 2(a) is a plan view of an alternative exemplary embodiment of a SAW sensor array substrate according to the present invention, and FIG. 2(b) is partial cross-sectional view taken along line A-A' of FIG. 2(a).

Figure 2:
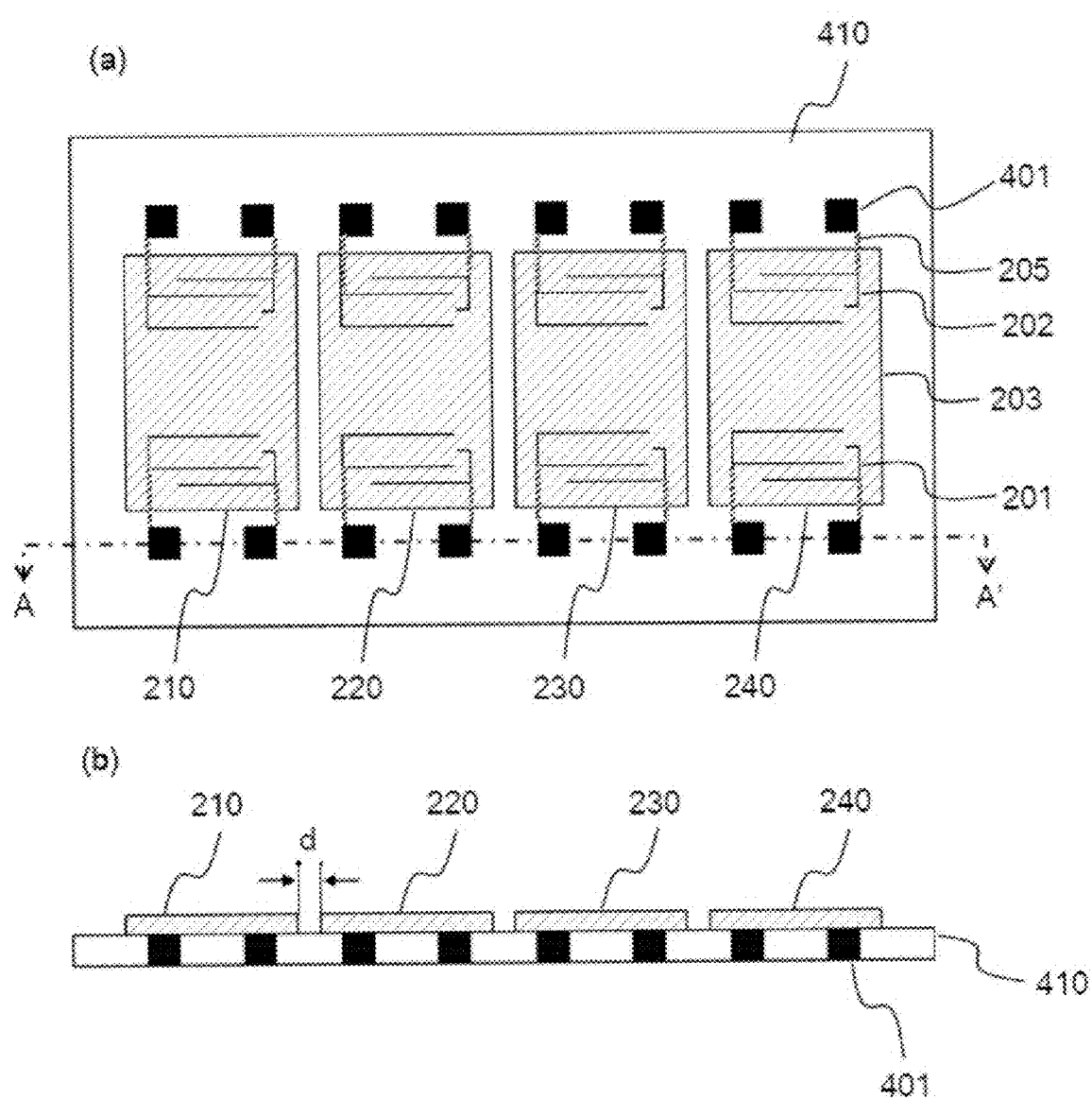
FIG. 2(a) is a plan view of an exemplary embodiment of a SAW sensor array substrate.
FIG. 2(b) is partial cross-sectional view taken along line A-A' of FIG. 2(a)

Referring to FIG. 2, in an alternative exemplary embodiment, four SAW sensors 210, 220, 230 and 240 are installed substantially in parallel to each other along an upper surface of a SAW sensor array substrate 410.

Each of the SAW sensors 210, 220, 230 and/or 240 includes a pair of inter-digital transducers ("IDTs") 201 and 202 disposed on the SAW sensor array substrate 410, which in an exemplary embodiment is formed of a piezoelectric material.

The piezoelectric material for forming the SAW sensor array substrate 410 includes a material having a characteristic in which an electrical signal is generated when a mechanical signal is applied (e.g., a piezoelectric effect), or generating a mechanical signal when an electrical signal is applied (e.g., a reverse piezoelectric effect). In an exemplary embodiment, the piezoelectric materials may include, for example, lithium niobate ($LiNbO_3$), lithium tantalite ($LiTaO_3$), lithium teraborate ($Li_2B_4O_7$), barium titanate ($BaTiO_3$), $PbZrO_3$, $PbTiO_3$, PZT, ZnO, GaAs, quartz and niobate.

The IDTs 201 and 202 of the pair of IDTs 201 and 202 are interfaces between electrical circuit and an acoustic delay line (not shown) and may be formed of, but are not limited to, a thin metal film of an aluminum alloy, a copper alloy or gold.

One IDT 201 of the pair of IDTs 201 and 202 generates a surface acoustic wave by a signal applied thereto, and thus will hereinafter be referred to as an "input IDT 201" or a "transmitter 201." The surface acoustic wave is delivered to the other IDT 202 of the pair of IDTs 201 and 202 by expansion and compression with a specific frequency along a surface of the SAW sensor array substrate 410, and is converted into an electrical signal due to the reverse piezoelectric effect. Thus, the IDT 202 will hereinafter be referred to as an "output IDT 202" or a "receiver 202."

Signals inputted and outputted from the input IDT 201 and the output IDT 202 are collected via electrical contacts using a pad 401, e.g., one of the connectors 401, disposed on the SAW sensor array substrate 410. In an exemplary embodiment, as shown in FIG. 2, the input IDT 201 and/or the output IDT 202 may be connected to respective pads 401 using a connecting wire 205.

As a distance d between the SAW sensors installed on the SAW sensor array substrate 410 decreases, waste of a sample to be senses is substantially reduced, as described in greater detail above. However, if the distance is too small, signal interference may occur between the SAW sensors 210, 220, 230 and 240. Thus, the distance d is appropriately adjusted in an exemplary embodiment. Moreover, the SAW sensors 210, 220, 230 and 240 may be arranged a uniform distance d apart from each other, as shown in FIGS. 2 and 3.

Figure 3:
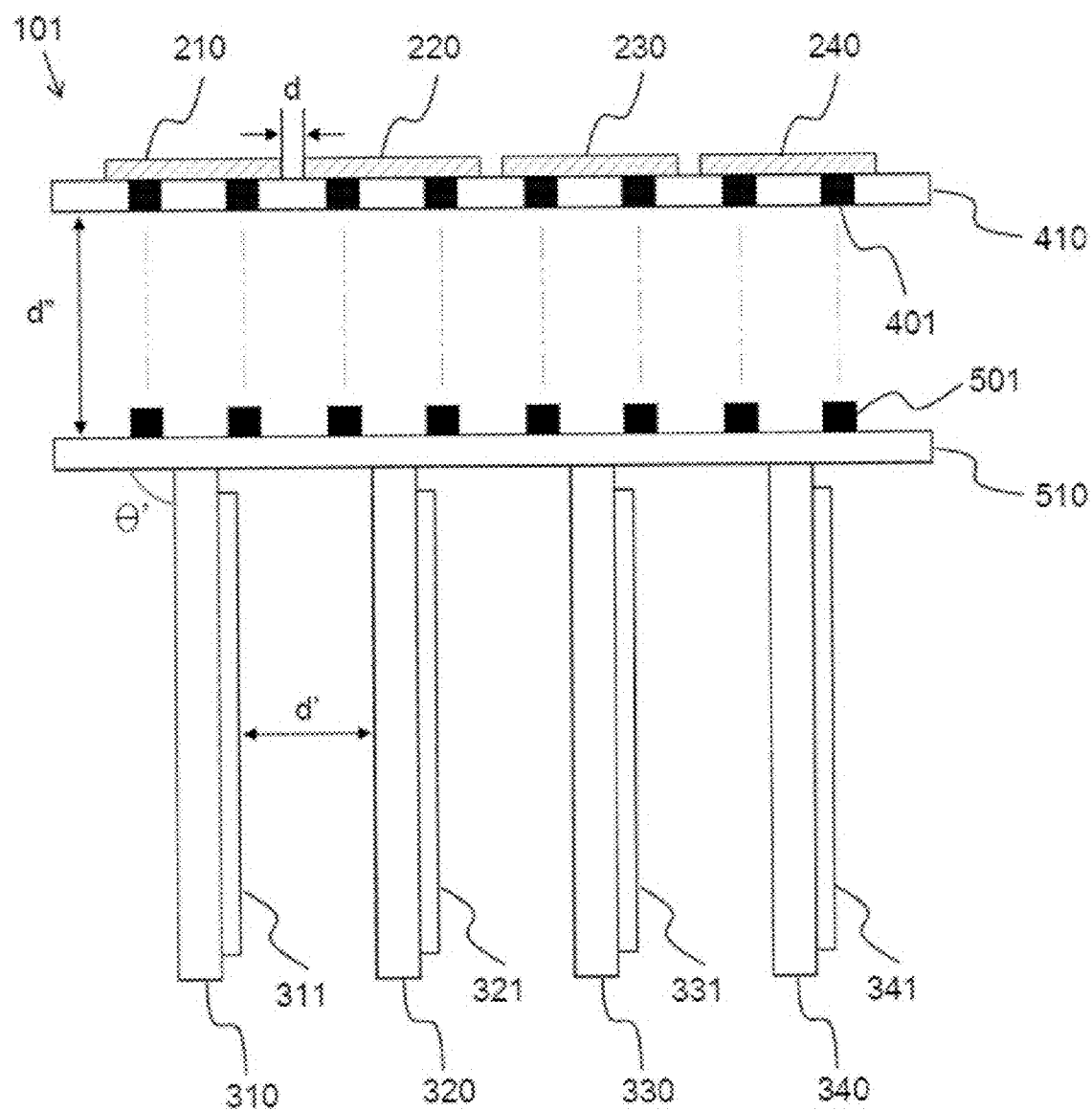
FIG. 3 is a partial cross-sectional view of an alternative exemplary embodiment of a SAW sensor device including the SAW sensor array substrate of FIGS. 2(a) and 2(b)

FIG. 3 is a partial cross-sectional view of an alternative exemplary embodiment of a SAW sensor device including the SAW sensor array substrate of FIGS. 2(a) and 2(b). More particularly, in FIG. 3, a partial cross-sectional view of a SAW sensor device 101 including the SAW sensor array substrate 410 of FIG. 2 is illustrated.

Referring to FIG. 3, the SAW sensor device 101 according to an alternative exemplary embodiment includes the SAW sensor array substrate 410 formed by arranging two or more SAW sensors, e.g., the SAW sensors 210, 220, 230 and 240, on a substrate, e.g., the SAW sensor array substrate 410, a top plate 510 disposed between the SAW sensor array substrate 410 and an oscillator (or two or more oscillators, e.g., oscillators 310, 320, 330 and 340). As shown in FIG. 3, the top plate 510 is substantially parallel to the SAW sensor array substrate 410. In addition, the oscillators 310, 320, 330 and 340 are connected to the top plate 510.

Thus, in an exemplary embodiment, the oscillators 310, 320, 330 and 340 are installed under, e.g., below, the SAW sensor array substrate 410 (as viewed in FIG. 3). The oscillators 310, 320, 330 and 340 correspond to the SAW sensors 210, 220, 230 and 240, respectively, on the SAW sensor array substrate 410.

The oscillators 310, 320, 330 and 340 may be directly connected to the SAW sensor array substrate 410 or, alternatively, may be indirectly connected thereto through the top plate 510 serving as a connector, as shown in FIG. 3.

The top plate 510, the SAW sensors 210, 220, 230 and 240 and the SAW sensor array substrate 410 are all installed substantially in parallel to each other, and a predetermined angle θ' between the top plate 510 and the oscillators 310, 320, 330 and 340 is an angle between the SAW sensors 210, 220, 230 and 240 and the oscillators 310, 320, 330 and 340. In an exemplary embodiment, the predetermined angle θ' may be from about 30° to about 270° or, alternatively, about 90°±30°, e.g., from about 60° to about 120°.

The SAW sensors 210, 220, 230 and 240 disposed on the SAW sensor array substrate 410, the top plate 510 and the oscillators 310, 320, 330 and 340 may be electrically connected via connectors 401 and 501.

More specifically, in an exemplary embodiment, the connectors 501 are disposed on an upper surface, e.g., a top surface (as viewed in FIG. 3), of the top plate 510 to be directly connected to the input IDT 201 (FIG. 2) and the output IDT 202 (FIG. 2) of each of the SAW sensors 210, 220, 230 and 240. In an alternative exemplary embodiment, other connectors (not shown) may also be disposed on a bottom surface of the top plate 510 to be connected to input/output connectors (not shown) of the oscillators 310, 320, 330 and 340.

In an exemplary embodiment, the connectors 501, disposed on the upper, e.g., top, surface of the top plate 510, are connected to pads 401, e.g., the connectors 401, disposed on the SAW sensor array substrate 410 to be connected to the input IDT 201 and the output IDT 202 (FIG. 2) of each of the SAW sensors 210, 220, 230 and 240.

As shown FIG. 3, a distance between the SAW sensors 210, 220, 230 and 240 and the oscillators 310, 320, 330 and 340 is effectively minimized, and connectors to be connected to the input IDT and the oscillator are formed in one body, while connectors to be connected to the output IDT and the output oscillator may be formed in one body, as well. However, it will be understood that, in alternative exemplary embodiments, the abovementioned connectors may be formed separately, and therefore included as separate members.

In an exemplary embodiment, the abovementioned connectors electrically connect the abovementioned components and, accordingly, may include metal interconnections, via holes and bonding wires, for example, but alternative exemplary embodiments are not limited thereto.

In an exemplary embodiment, a distance d' between the oscillators 310, 320, 330 and 340 is not particularly limited, is within a range of values in which signal interference does not occur. In addition, to further reduce signal interference, shielding devices 311, 321, 331 and 341 may be disposed between the oscillators 310, 320, 330 and 340, respectively, as shown in FIG. 3. It will be noted that, as shown in FIG. 3, in an exemplary embodiment including the shielding devices 311, 321, 331 and 341, the distance d' between the oscillators 310, 320, 330 and 340 is reduced by an amount equal to a thickness of the shielding devices 311, 321, 331 and 341.

The shielding devices 311, 321, 331 and 341 may include a buffering material. The shielding devices 311, 321, 331 and 341 are installed between the oscillators 310, 320, 330 and 340, respectively, and may be disposed on only one surface of each of the oscillators 310, 320, 330 and 340, as shown in FIG. 3. Thus, a number of the shielding devices may be equal to or less than a number (n) of oscillators. In an exemplary embodiment, the number of shielding devices may be n or, alternatively, may be n−1. The shielding devices 311, 321, 331 and 341 are not limited to any particular structures, and the shielding devices 311, 321, 331 and 341 substantially reduce and/or effectively prevent interference between the oscillators 310, 320, 330 and 340, and thus may have a structure substantially surrounding a horizontal plane of each of the oscillators 310, 320, 330 and 340, since vibrations may be generated from the oscillators 310, 320, 330 and 340 and delivered along surfaces thereof.

Figure 4:
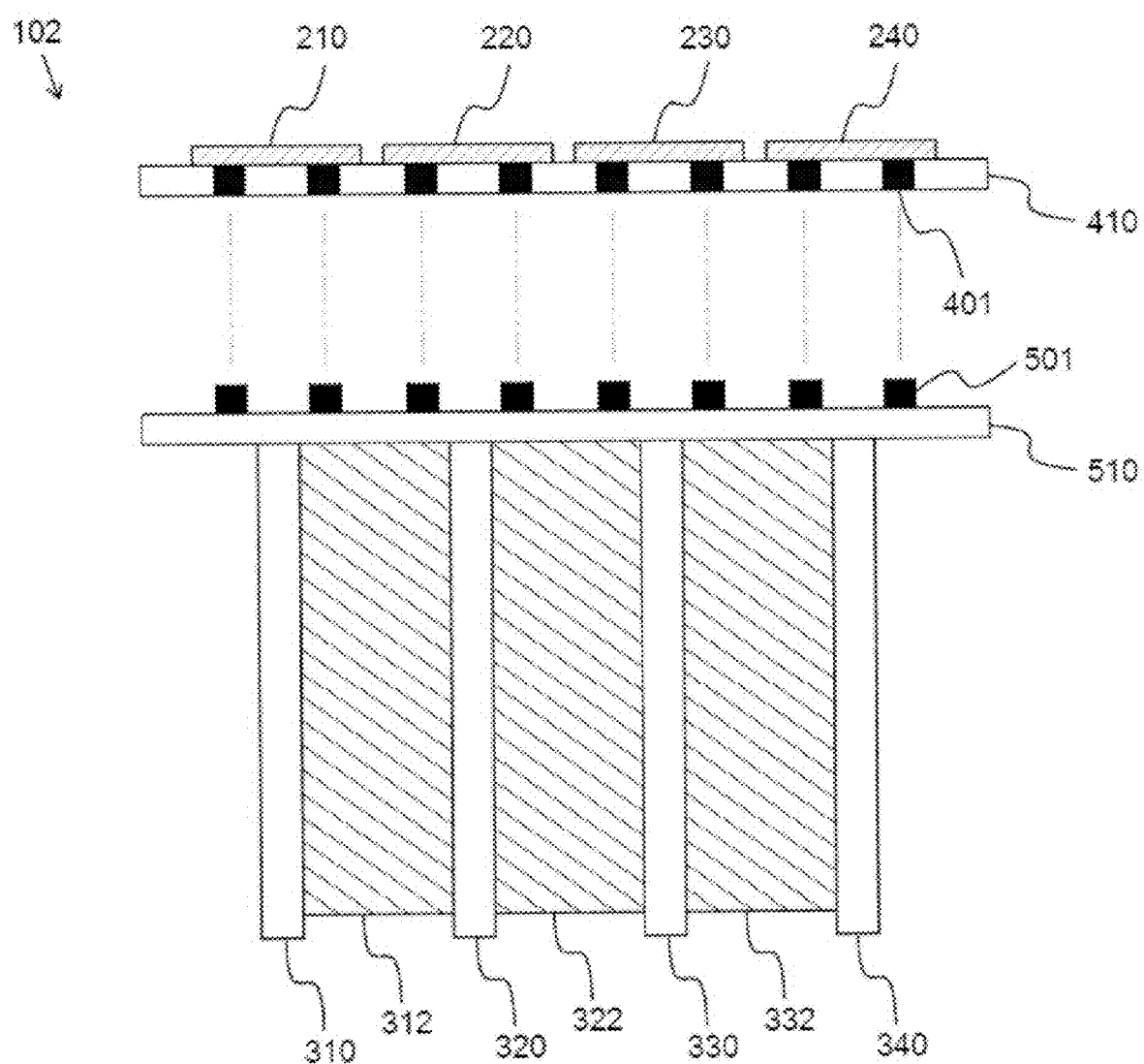
FIG. 4 is a partial cross-sectional view of another alternative exemplary embodiment of a SAW sensor device.

In an alternative exemplary embodiment, shielding devices 312, 322, 332 and 342 may include a structure which substantially fills the distance d' between the oscillators 310, 320, 330 and 340, respectively, as shown in FIG. 4, which is a partial cross-sectional view of an alternative exemplary embodiment of a SAW sensor. Accordingly, fixation of the oscillators is substantially improved, and the oscillators are therefore stably installed in a SAW sensor device 102 according to an exemplary embodiment.

Referring again to FIG. 3, in another exemplary embodiment, the distance d between the SAW sensors 210, 220, 230 and 240 and the distance d' between the oscillators 310, 320, 330 and 340 may be uniform. For example, the distances d and d' may be disposed at uniform intervals having error ranges less than about 5% or, alternatively, less that about 10%.

In addition, a distance between the SAW sensors 210, 220, 230 and 240 and the oscillators 310, 320, 330 and 340 may also be uniform, and when the top plate 510 and/or the SAW sensor array substrate 410 are disposed between the SAW sensors 210, 220, 230 and 240 and the oscillators 310, 320, 330 and 340, they may be spaced a uniform distance d" apart from each other, but alternative exemplary embodiments are not limited thereto. For example, in an alternative exemplary embodiment, the SAW sensors 210, 220, 230 and 240 and the oscillators 310, 320, 330 and 340 may be in direct contact with each other.

The SAW sensor array substrate 410 may include, but is not limited to, a ceramic substrate. In an exemplary embodiment, the SAW sensor array substrate 410 is not formed separately from the SAW sensors 210, 220, 230 and 240, but may instead be formed in one body including both the SAW sensor array substrate 410 and the SAW sensors 210, 220, 230 and 240. In addition, a plurality of IDT pairs (FIG. 2) may be disposed at regular intervals on the SAW sensor array substrate 410, which in and exemplary embodiment is formed of a piezoelectric material, and thus the SAW sensors 210, 220, 230 and 240 may be formed as one body with the SAW sensor array substrate 410.

In alternative exemplary embodiments, the SAW sensor devices 100, 101 and 102 may include signal detectors (not shown) which detect signals outputted from the SAW sensors 210, 220, 230 and 240 and/or the oscillators 310, 320, 330 and 340.

Moreover, the SAW sensor devices 101 and 102 according to alternative exemplary embodiments may be fabricated by arranging the SAW sensors 210, 220, 230 and 240 on the SAW sensor array substrate 410, connecting the plurality of oscillators 310, 320, 330 and 340 to have a predetermined angle under the top plate 510, the connector 501 being disposed on the top plate 510 to correspond to the pad 401 of the SAW sensor array substrate 410, and connecting the connector 501 of the top plate 510 connected to the oscillator to the pad 401 of the SAW sensor array substrate 410 on which the SAW sensors 210, 220, 230 and 240 are arranged.

In an exemplary embodiment, the top plate 510 may be connected to the SAW sensor array substrate 410, on which the SAW sensors 210, 220, 230 and 240 are disposed, and the oscillators 310, 320, 330 and 340 may be connected to the top plate 510, as shown in FIGS. 3 and 4.

The SAW sensor devices 100, 101 and 102 according to exemplary embodiments described herein analyze mass, pressure, density and/or viscosity of a material bound to the SAW sensors 210, 220, 230 and 240 by detecting a change in a signal outputted from the oscillators 310, 320, 330 and 340.

In an exemplary embodiment of driving the SAW sensor devices 100, 101 and 102, an electrical signal is converted into a mechanical wave through an IDT on the SAW surface, for example. The wave is changed by physical, chemical and/or electrical reactions between a receptor on the SAW sensor surface and a target material. Accordingly, a center frequency, phase or size of an output signal of the SAW sensor is changed. Therefore, observation of the change in the signal induces detection of the target material bound to the SAW sensor, and further qualitative and quantitative analyses of an object material may be performed.

Thus, exemplary embodiments may also be used in analyzing and monitoring the target material included in a sample of a biological fluid, such as a chemical fluid or a body fluid, for example.

More specifically, for example, the SAW sensor devices 100, 101 and 102 according to exemplary embodiments may be used as biosensors configured to detect a biological material, but alternative exemplary embodiments are not limited thereto. The biosensor may include a measurement sensor using biological materials such as enzymes, bacteria and live tissues, for example, a measurement system sensor imitating a mechanism in a living system, and a measurement sensor for living systems.

Additionally, a biosensor using a SAW sensor may obtain a greater change in frequency than a conventional biosensor, be applicable for implementation in both liquid and gas phases, and may have an aftershock frequency which is a maximum of about 10 times greater than in the conventional biosensor. Thus, the biosensor according to exemplary embodiments provides substantially improved integration, fabrication, real-time measurement and measurement of a small amount of sample.

The biosensor according to an exemplary embodiment may detect a disease, for example, using a SAW sensor on which a receptor specifically responding to the specific disease is applied. More specifically, the detection of the disease may be determined based on whether or not a specimen obtained from a patient responds to the receptor on the SAW sensor. Accordingly, the biosensor uses expensive samples, and if the specimen is obtained from a patient, an available amount of the sample is limited.

Thus, in an exemplary embodiment, to conduct fast and numerous tests using a biosensor, a plurality of the SAW sensors may be used, but in this case, an increased amount of sample is needed.

However, according to the exemplary embodiments described herein, even when the plurality of SAW sensors is included, waste of the sample is substantially reduced by substantially reducing a distance between the SAW sensors. Accordingly, fast and numerous tests may be conducted even with a limited amount of sample.

In an Example, three SAW sensors were disposed on one substrate to form a SAW sensor array, and a connector on a top plate substantially perpendicularly connected to an oscillator was connected to a pad of the SAW sensor array, thereby fabricating a SAW sensor device. Antigens (rabbit IgG) responding to antibodies (anti-rabbit IgG) were applied as receptors to surfaces of a first SAW sensors (first sample SAW 1) and a second SAW sensor (second sample SAW 2), but receptors were not applied to a surface of a third SAW sensor (reference SAW).

A spring pin was used as the connector, and an MCX (micro coaxial) was used as a connector connecting an output signal to a detector.

In an Experimental Sample, a sample containing antibodies of 10 ug/ml as target materials was prepared. Vibration was applied to the SAW sensor according to the Example described above, to confirm that a reference frequency was 176 megahertz (MHz). After 100 seconds, a sample was injected to obtain a sensing result, which is shown in FIG. 5, which is a graph of frequency, in Hertz (Hz) versus time, in seconds (sec) illustrating comparative test results of the Experimental Examples of SAW sensors described above, e.g., SAW sensors with and without receptors.

Figure 5:
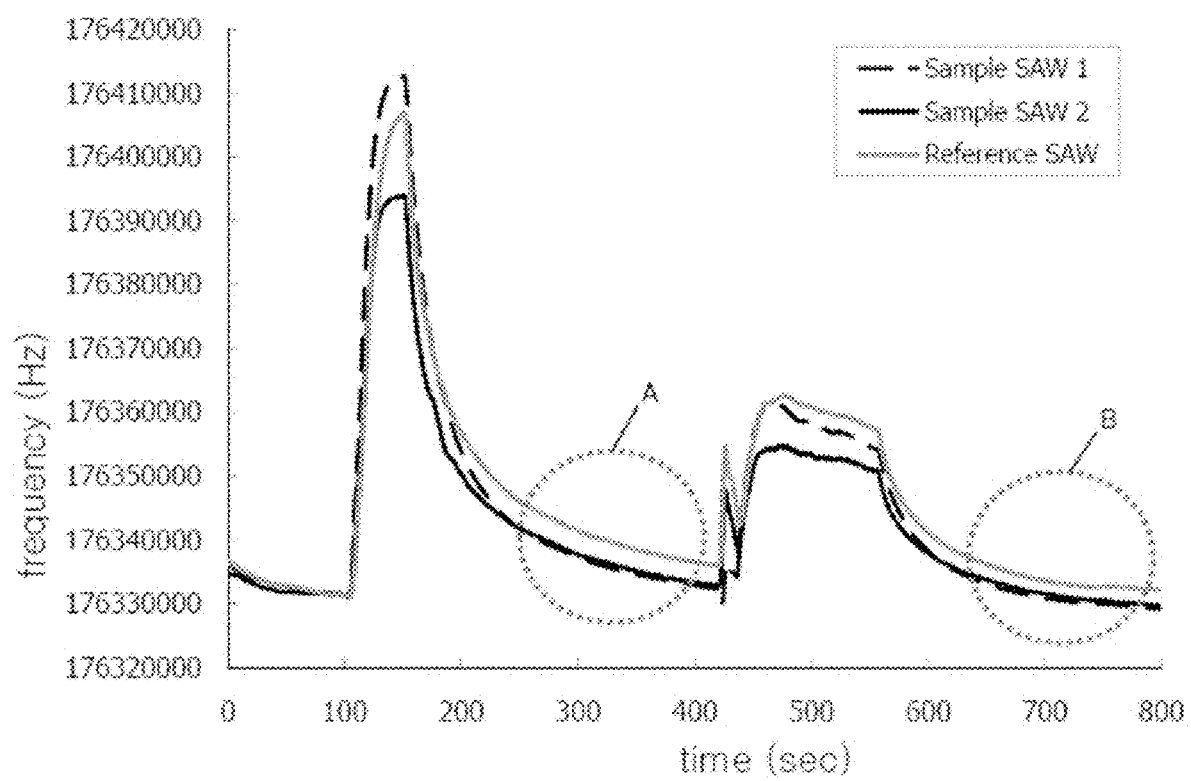
FIG. 5 is a graph of frequency versus time illustrating comparative test results of experimental examples of SAW sensors with and without receptors.

Referring to FIG. 5, as the sample was injected at 100 seconds after the application of the vibration, frequencies of all three SAWs (e.g., Sample SAW 1, Sample SAW 2 and the Reference SAW) increased, due to a pressure gradient, and then stabilized. Accordingly, the frequencies of the sample SAWs reacting with the target material became much lower than that of the reference SAW reacting with none. Referring to portion "A" of FIG. 5, it can be seen that there was no difference between signals in the first sample SAW 1 and the second sample SAW 2. After 410 seconds, the samples were washed, and it can be seen from portion "B" that, after washing, the samples showed a similar result as in the first measurement described above (in portion "A" of FIG. 5).

Thus a SAW sensor device according to exemplary embodiments includes an oscillator disposed not parallel to a SAW sensor, but instead inclined at a predetermined angle with respect to the SAW sensor. As a result, an increase in distance between SAW sensors due to a width of the oscillator is substantially reduced and/or is effectively prevented or minimized. Accordingly, waste of a sample is substantially reduced. In addition, signal interference and generation of noise is substantially reduced even when using an oscillation technique, resulting in substantially increases in sensitivity, as well as economical and/or industrial efficiencies.

The present invention should not be construed as being limited to the exemplary embodiments set forth herein. Rather, these exemplary embodiments are provided so that this disclosure will be thorough and complete and will fully convey the concept of the present invention to those skilled in the art While the present invention has been particularly shown and described with reference to exemplary embodiments thereof, it will be understood by those of ordinary skill in the art that various changes in form and details may be made therein without departing from the spirit or scope of the present invention as defined by the following claims.

What is claimed is:

1. A surface acoustic wave sensor device comprising:
   a surface acoustic wave sensor; and
   an oscillator corresponding to the surface acoustic wave sensor,
   wherein a horizontal plane defined by the oscillator is inclined at a predetermined angle with respect to a horizontal plane defined by the surface acoustic wave sensor, the predetermined angle being greater than zero degrees.

2. The surface acoustic wave sensor device of claim 1, further comprising:
   two or more of the surface acoustic wave sensors; and two or more of the oscillators, wherein each oscillator of the two or more oscillators corresponds to a surface acoustic wave sensor of the two or more surface acoustic wave sensors.

3. The surface acoustic wave sensor device of claim 1, wherein the predetermined angle is from about 30 degrees to about 270 degrees.

4. The surface acoustic wave sensor device of claim 1, wherein the predetermined angle is from about 60 degrees to about 120 degrees.

5. The surface acoustic wave sensor device of claim 1, wherein the surface acoustic wave sensor comprises:
 a substrate formed of a piezoelectric material; and
 a pair of inter-digital transducers, the pair of inter-digital transducers including an input inter-digital transducer and an output inter-digital transducer.

6. The surface acoustic wave sensor device of claim 2, further comprising:
 a surface acoustic wave sensor array substrate on which the two or more surface acoustic wave sensors are disposed; and
 a top plate disposed between the surface acoustic wave sensor array substrate and the two or more oscillators and disposed substantially parallel to the surface acoustic wave sensor array substrate, wherein the two or more oscillators, corresponding to the two or more surface acoustic wave sensors, are electrically connected to the top plate.

7. The surface acoustic wave sensor device of claim 6, wherein
 the two or more surface acoustic wave sensors are disposed above the top plate, and
 the two or more oscillators are disposed under the top plate.

8. The surface acoustic wave sensor device of claim 6, wherein the surface acoustic wave sensor array substrate, the top plate and the two or more oscillators are electrically connected via connectors.

9. The surface acoustic wave sensor device of claim 6, wherein the surface acoustic wave sensor array substrate and the two or more oscillators are directly connected to each other without connectors.

10. The surface acoustic wave sensor device of claim 6, further comprising:
 connectors disposed on an upper surface of the top plate; and
 connectors disposed on a lower surface of the top plate, wherein
 the connectors disposed on the upper surface of the top plate connect the input inter-digital transducer and the output inter-digital transducer, and
 the connectors disposed on the lower surface of the top plate are connected to input-output connectors of the two or more oscillators.

11. The surface acoustic wave sensor device of claim 2, further comprising shielding devices disposed between each of the two or more oscillators.

12. The surface acoustic wave sensor device of claim 2, wherein distances between each of the two or more surface acoustic wave sensors and each of the two or more oscillators are equal.

13. The surface acoustic wave sensor device of claim 6, wherein the surface acoustic wave sensor array substrate is disposed at one of a uniform distance apart from the top plate and in contact with the top plate.

14. A method of fabricating a surface acoustic wave sensor device, the method comprising:
 providing a surface acoustic wave sensor array substrate;
 arranging surface acoustic wave sensors on the surface acoustic wave sensor array substrate;
 connecting oscillators to a top plate, the top plate disposed substantially parallel to the surface acoustic wave sensor array substrate; and
 connecting each of the surface acoustic wave sensors to a corresponding one of the oscillators,
 wherein a horizontal plane defined by each of the oscillators is inclined at a predetermined angle with respect to a horizontal plane defined by each of the surface acoustic wave sensors, the predetermined angle being greater than zero degrees.

* * * * *